United States Patent [19]

Fujishiro et al.

[11] 4,076,608
[45] Feb. 28, 1978

[54] OXYGEN SENSOR

[75] Inventors: Takeshi Fujishiro; Toru Kita, both of Yokohama, Japan

[73] Assignee: Nissan Motor Company, Limited, Yokohama, Japan

[21] Appl. No.: 739,020

[22] Filed: Nov. 4, 1976

[51] Int. Cl.² ............................................. G01N 27/46
[52] U.S. Cl. ............................. 204/195 S; 174/74 R; 174/94 R; 339/177 R
[58] Field of Search ...................... 204/1 S, 195 S; 174/74 R, 94 R; 339/177 R, 177 E, 177 L

[56] References Cited

U.S. PATENT DOCUMENTS

| 2,757,351 | 7/1956 | Klostermann | 339/177 R |
|---|---|---|---|
| 3,033,600 | 5/1962 | Drysdale | 174/94 R |
| 3,439,294 | 4/1969 | Flanagan et al. | 339/177 R |
| 3,578,578 | 5/1971 | Von Krusenstierna | 204/195 S |
| 3,844,920 | 10/1974 | Burgett et al. | 204/195 S |
| 3,891,529 | 6/1975 | Beesch | 204/195 S |
| 3,960,692 | 6/1976 | Weyl et al. | 204/195 S |
| 3,960,693 | 6/1976 | Weyl et al. | 204/195 S |
| 4,019,974 | 4/1977 | Weyl et al. | 204/195 S |

*Primary Examiner*—T. Tung
*Attorney, Agent, or Firm*—Bacon & Thomas

[57] ABSTRACT

An oxygen sensor comprises an electrolyte which is shaped into a conical tube having a closed end of small diameter and an open end of large diameter. The wall thickness of the electrolyte is gradually decreased toward the closed end from the open end and that of the closed end is 0.3 to 1.0 mm so as to provide a high sensitivity.

11 Claims, 7 Drawing Figures

OXYGEN SENSOR

BACKGROUND OF THE INVENTION

The present invention relates in general to a sensor and more particularly to a measuring cell for determining oxygen concentration in a gas mixture flowing through a tube.

In connection with the problem of reducing air pollution resulting from the automobile internal combustion engine, it is well known that if the air to fuel ratio of the intake charge to the engine is maintained at or near stoichiometric condition during most modes of operation, the exhaust gases will contain less harmful components, i.e., hydrocarbons (HC), carbon monoxide (CO) and nitrogen oxides ($NO_x$). For controlling the air to fuel ratio of the intake charge at the stoichiometric condition, a so-called closed loop system having an oxygen sensor placed in communication with the exhaust gases issued from the engine has been widely used. The oxygen sensor is constructed to generate an electrical signal responsive to the oxygen content of the exhaust gases. The electrical signal in turn is received in a control means connected to the engine for regulating or varying the charactor of the intake air-fuel charge so as to maintain the charge at the stoichiometric condition.

Hitherto, stabilized zirconium oxide ($ZrO_2$) has been widely employed as a main element of the oxygen sensor. As is well known, the stabilized zirconium oxide ($ZrO_2$) exhibits conductivity by means of oxygen ions which transfer therethrough. In reality, if some gas mixture whose partial oxygen pressure or absolute oxygen pressure must be measured is present on one side of a partition member made of the zirconium oxide, and simultaneously, a reference gas having a known partial oxygen pressure is present on the other side, a considerable voltage difference (E) is generated by the movement of the oxygen ions between the one and the other sides of the partition member. The magnitude of the voltage difference (E) is generally estimated by the next Nernst equation;

$$E = \frac{RT}{4F} \ln \frac{P_1}{P_2} \quad (1)$$

where:
- $R$ ... gas constant
- $T$ ... absolute temperature
- $F$ ... Faraday constant
- $P_1$ ... partial oxygen pressure of the reference gas
- $P_2$ ... partial oxygen pressure of the unknown gas mixture With this equation, it will be appreciated that the partial oxygen pressure of the unknown gas mixture and accordingly the oxygen concentration of the same are calculated by measuring the voltage difference (E). By the way, it was revealed that the oxygen concentration of the exhaust gases issued from the engine is critically dependent upon the air to fuel ratio of the intake charge to the engine.

Apart from this, it has been observed that the zirconium oxide oxygen sensor does not generate sufficient voltage difference at low temperature. In fact a sufficient voltage difference for measuring the oxygen concentration cannot be expected at a temperature below about 350° C. Therefore, when equipped in the exhaust tube of the engine, the zirconium oxide oxygen sensor must be located in a position where a highest possible temperature of the exhaust gases from the engine exists. FIG. 2 shows the distribution of temperature in the exhaust tube in a case where the displacement of the associated engine is 2000 cc and the inside diameter of the exhaust tube is 45 mm. The curves $a$ and $b$ represent the respective temperature distribution in two cases wherein the engine speeds are 1200 rpm and 800 rpm, respectively. From this Figure, it will be noted that in the exhaust tube, a temperature difference ranging from about 150° C to about 200° C will appear in each engine operation mode. Furthermore, the temperature gradient is maximum in a region between the inner surface of the exhaust tube and a portion about 10 mm away from the inner surface of the tube. These phenomena similarly occur also in other cases wherein the displacement of the engine changes from about 1000 cc to about 4000 cc and the inside diameter of the exhaust tube changes from about 40 to 60 mm. From this description, it will be appreciated that the zirconium oxide oxygen sensor should be arranged in such a manner that the sensitive part thereof is located in a position at least 10 mm away from the inner surface of the exhaust tube.

SUMMARY OF THE INVENTION

Therefore, it is a first object of the present invention to provide an improved oxygen sensor which has a very sensitive part located in a position where a highest possible temperature of the exhaust gases exists.

It is a second object of the present invention to provide an improved oxygen sensor which comprises a tubular electrolyte having one closed end projecting into the interior of the exhaust tube and the other open end mounted in a holder connected to the exhaust tube.

It is a third object of the present invention to provide an improved oxygen sensor which comprises a tubular electrolyte, of stabilized zirconium oxide, having a closed end wall the thickness of which is about 0.3 to 1.0 mm, the closed end being projected into the interior of the exhaust tube.

It is a fourth object of the present invention to provide an improved oxygen sensor having an extending portion of at least 12 mm, the extending portion being projected into the interior of the exhaust tube so as to be adequately exposed to the exhaust gases emitted from the engine.

It is a fifth object of the present invention to provide an improved oxygen sensor comprising a tubular electrolyte having a closed end and an open and, the wall thickness of the electrolyte being gradually decreased toward the closed end from the open end.

It is a sixth object of the present invention to provide an improved oxygen sensor which comprises a tubular electrolyte having on its surfaces smoothly rounded off sections for facilitating the operation of the platinum coating on the surfaces of the electrolyte.

It is a seventh object of the present invention to provide an improved oxygen sensor which comprises a tubular electrolyte and terminal means, the terminal means being disposed in an open end of the electrolyte so as to provide an effective electrical connection between them.

BRIEF DESCRIPTION OF THE DRAWINGS

Other objects and advantages of the present invention will be more apparent from the description when taken in conjunction with the accompanying drawings, in which.

DETAILED DESCRIPTION OF PREFERRED EMBODIMENTS

Figure 1:
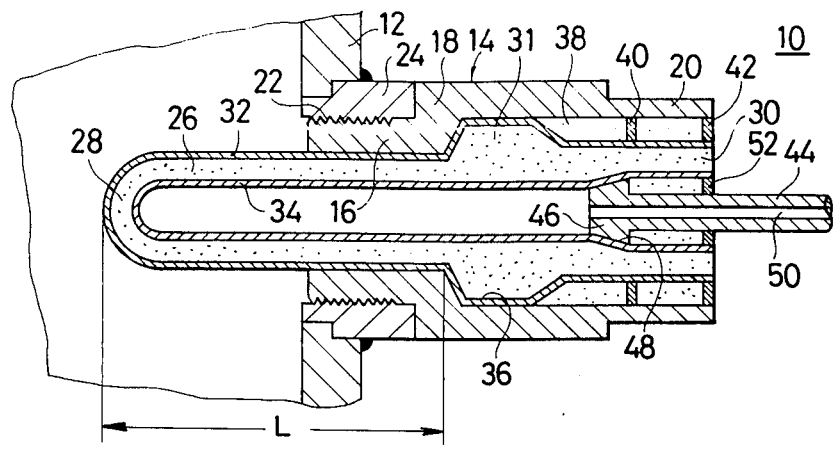
FIG. 1 is a sectional view of a conventional oxygen sensor, the sensor being shown fixed to an exhaust tube of an engine system.
Figure 2:
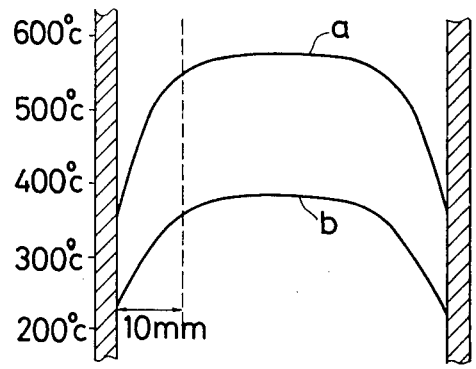
FIG. 2 is an illustration showing the distribution of temperature provided in the exhaust tube.

In order to clearly define the inventive steps of the present invention over the prior art, a detailed description of one of the conventional oxygen sensors will be given with the aid of FIG. 1.

In this Figure, the conventional oxygen sensor is generally designated by the numeral 10 and is shown accompanied with an exhaust tube 12 through which exhaust gases issued from an engine, i.e., an internal combustion engine, flow.

The oxygen sensor 10 comprises an outer cylindrical holder 14 of metal having an externally threaded portion 16 terminating in a radial shoulder portion 18 and a relatively thin plate tube portion 20 extending outwardly from the radial shoulder portion 18. The radial shoulder portion 18 is used for facilitating acceptance and seating of the outer cylindrical holder 18 in a threaded bore 22 formed in an annular connector 24 which has been firmly connected to the exhaust tube 12 by welding.

Disposed in the outer cylindrical holder 14 while projecting at its leading portion into the interior of the exhaust tube 12 is a solid state oxygen sensitive electrolyte 26 which is formed into a generally cylindrical structure having a closed end 28, an open end 30 and having at its generally middle portion a radially outwardly raised portion 31. As shown, the closed end 28 is located in or projected into the interior of the exhaust tube 12. The electrolyte 26 comprises zirconium dioxide ($ZrO_2$) and and stabilizer, such as calcium oxide (CaO). Now, it should be noted that the wall thickness of this conventional electrolyte 28 is generally uniform in the section between the closed end 28 and the raised portion 31, as shown. The outer and inner surfaces of the cylindrical electrolyte 26 are covered or coated with first and second platinum electrodes 32 and 34 which are electrically insulated from each other. The electrolyte 26 with the first and second platinum electrodes 32 and 34 is disposed in the outer cylindrical holder 14 in such a manner that the radially outwardly raised position 31 thereof is snugly fitted in an enlarged bore 36 formed in the holder 14. Thus, the axial movement of the electrolyte 26 toward the inside of the exhaust tube 12 relative to the holder 14 is prevented and simultaneously, the electrical connection between the holder 14 and the first platinum electrode 32 is provided. A space (no numeral) defined between the holder 14 and the first platinum electrode 32 and extending from the raised portion 31 to the open end 30 of the electrolyte 26 is filled or packed with an electrically conductive powder 38 such as copper, aluminum and/or graphite powder, so that the electrical connection between the outer holder 14 and the first platinum electrode 32 is effectively made. Within the space for the powder 38 are tightly disposed spaced first and second conductive rings 40 and 42 which can more effectively provide the electrical connection between the holder 14 and the first platinum electrode 32 while steadily supporting the electrolyte 26 in the holder 14. A connecting rod 44 is secured at its enlarged head portion 46 to the second platinum electrode 34 located on a stepped portion 48 formed at the inner surface of the electrolyte 26 near the open end 30. The connecting rod 44 is formed with an axially extending passage 50 for providing a fluid communication between the interior of the electrolyte 26 and the atmosphere. A space (no numeral) defined between the second platinum electrode 34 and the connecting rod 44 and extending from the enlarged head portion 46 to the open end of the electrolyte 26 is also filled or packed with the above-mentioned electrically conductive powder. A third conductive ring 52 is tightly disposed in this space for achieving effective electrical connection between the second platinum electrode 34 and the connecting rod 44.

By the way, in such a conventional oxygen sensor, it has been usually observed that the length (L) of a portion defined between the tip of the electrolyte 26 and the leading edge of the raised portion 31 is determined about 25 to 30 mm, and the wall thickness of the portion is about 2 to 3 mm. With this construction, however, the following several problems have arisen.

(1) When such conventional oxygen sensor is subjected to a so-called thermal shock cycling test in which (800° C × 3 minutes – 25° C × 1 minute) composes one cycle, a lot of hair-shaped cracks appear on the closed end of the electrolyte 26 and on the leading edge of the raised portion 31 before the test proceeds to five cycles. This means that the thermal shock resistance of this conventional electrolyte is very poor.

(2) Because the closed end and its neighborhood of the electrolyte 26 are constructed to have the large wall thickness throughout thereof, the inner impedance of the electrolyte 26 is undesirably increased. Usually, several MΩ resistance is provided to the electrolyte 26 at about 400° C. Furthermore, because of its large wall thickness of the electrolyte, it takes a relatively long time to warm up the electrolyte. Consequently, both the sensitivity of the oxygen sensor 10 and the lasting quality of the same are undesirably decreased.

Therefore, as mentioned before, the present invention is proposed to provide an improved oxygen sensor which can eliminate such drawbacks and disadvantages encountered in the conventional oxygen sensor.

Figure 3:
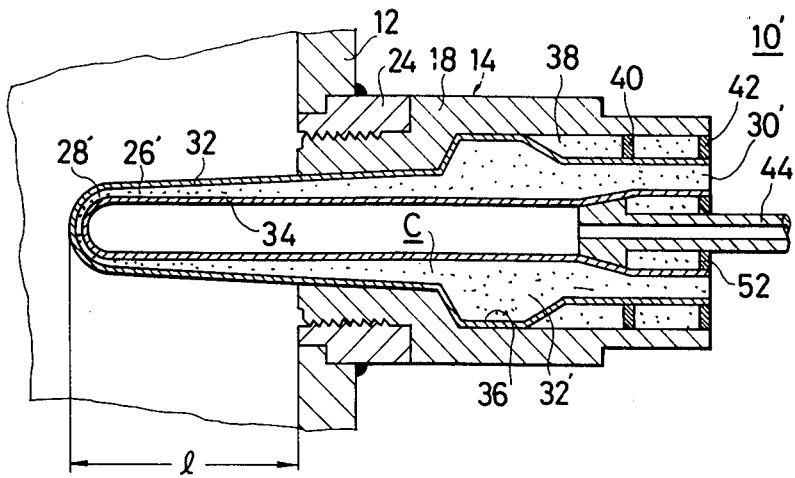
FIG. 3 is a sectional view of a first preferred embodiment of the oxygen sensor according to the present invention.

Referring to FIG. 3 of the drawings, there is illustrated a first preferred embodiment of the present invention. The oxygen sensor 10' of this embodiment comprises generally the same parts or elements as in the case of the above-mentioned conventional one (FIG. 1). As shown in this drawing, the electrolyte 26' is formed into a generally conical tube with a closed end 28' of small diameter and an open end 30' of large diameter. The wall thickness of the electrolyte 26' is gradually decreased toward the closed end 28' from the radially outwardly raised portion 32' snugly coupled in the bore 36 formed in the outer cylindrical holder 14. Now, it should be noted that the wall thickness of the closed end 28' is determined about 0.3 to 1.0 mm, and the wall thickness of a portion, indicated by the letter c, adjacent the left leading edge of the raised portion 32' is determined about 2 to 5 mm. In addition, the unit consisting of the electrolyte 26' and the first and second platinum electrodes 32 and 34 is so constructed to have an exhaust gas exposed portion which has at least 12 mm axial length (l) so that the thin closed end 28' can be located in the hot zone in the exhaust tube 12.

With this construction, the oxygen sensor 10' can operate optimally with increase of the sensitivity and the lasting quality thereof.

Several experiments have revealed that the thermal shock resistance of the subject electrolyte 26' is remarkably increased. More specifically, under the before-mentioned thermal shock cycling test, no cracks appear on the electrolyte 26' even when the test proceeds to 20 cycles. Furthermore, the inner impedance of the subject electrolyte 26' is preferably reduced to about 10 to 25% the impedance of the conventional one shown in FIG. 1. In addition, the warming up time of the oxygen sensor 10' is reduced to about 60 to 70% the time of the conventional sensor.

Figure 4A:
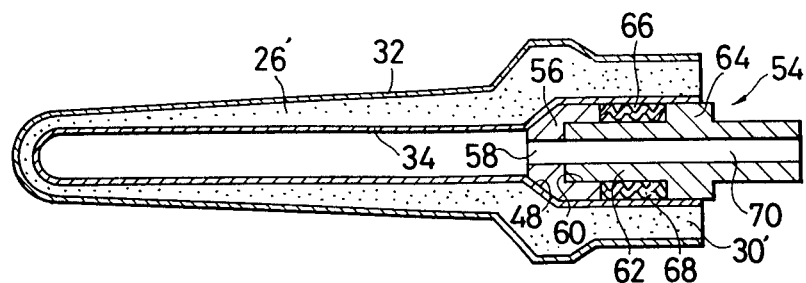
FIGS. 4A and 4B are sectional views of main parts of the second preferred embodiment of the oxygen sensor according to the present invention.
Figure 4B:
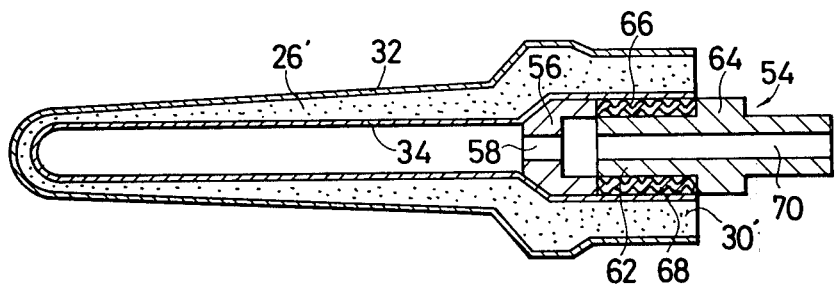

Referring to FIGS. 4A and 4B, there is shown an electrolyte, having similar construction to the electrolyte 26' of the first embodiment, to which an improved connecting means 54 is engaged. The connecting means 54 comprises an enlarged annular head member 56 having a through hole 58 and a female portion 60. As shown, the annular head member 56 is snugly engaged to the stepped portion 48 formed in the electrolyte 26' so that the female portion 60 faces the open end 30' of the electrolyte 26'. An elongate member 62 having a circular cross section and having at its generally middle portion a radially outwardly raised portion 64 is snugly engaged at one end or male portion thereof with the female portion 60 of the head member 56 while tightly contacting at the raised portion 64 with the second platinum electrode 34 at the open end thereof. A space 66 defined between the second platinum electrode 34 and the elongate member 62 and extending from the head member 56 to the outwardly raised portion 64 contains therein a corrugated cylindrical member 68 made of copper, or the like. The corrugated cylindrical member 68 is arranged in such a manner that when the elongate member 62 is moved toward the enlarged head member 56 to be secured to each other, the corrugated cylindrical member 68 is compressed urging the corrugations into electrical contact with the outer surface of the elongate member 62 and the inner surface of the second platinum electrode 34. The elongate member 62 has an axially extending through hole 70 which is to be connected with the above-mentioned through hole 58 of the head member 56 when the elongate member 62 is secured to the head member 56. FIG. 4B shows a state wherein the elongate member 62 is about to engage with the head member 56. It should be noted that before being compressed in the space 66, the corrugated cylindrical member 68 has maximum outside diameter slightly smaller than the inside diameter of the open end portion of the electrolyte 26', and minimum inside diameter slightly larger than the outside diameter of the elongate member 62. With this, the insertion of the corrugated cylindrical member 68 into the space 66 is facilitated.

With this construction, the following merits and advantages will arise. First, the radially outward and radially inward movements of the corrugations on corrugated cylindrical member 68 due to the compression thereof produce not only tight connection between the electrolyte 26' and the connecting means 54 but also reliable electrical contact between the second platinum electrode 34 and the connecting means 54. Second, since the radially outward and radially inward movements of the corrugations on the corrugated cylindrical member 68 can be controlled by the urging force applied thereto by the inward movement of the elongate member 62, the small variations in diameter of two portions between which the corrugated cylindrical member 68 is disposed are easily compensated.

Figure 4C:
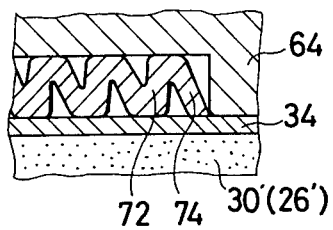
FIG. 4C is an enlarged sectional view of a slightly modified electrically conducting means employable in the oxygen sensor of the present invention.

If desired, as shown in FIG. 4C, each of the corrugations on the corrugated cylindrical member 68 may be formed so that the cross section of the corrugations has a generally saw-tooth section, the combination of the perpendicular and slanted portions 72 and 74 endowing the corrugated cylindrical member 68 with improved mechanical connection between the electrolyte 26' and the connecting means 54.

Figure 5:
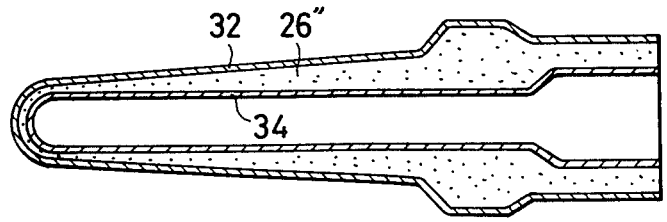
FIG. 5 is a sectional view of main parts of a third preferred embodiment of the oxygen sensor according to the present invention.

Referring now to FIG. 5 of the drawings, there is shown an electrolyte 26" which is slightly modified in shape. As shown, each of curved portions formed on the outer and inner surfaces of the electrolyte 26" is smoothly rounded off. Preferably, the radius of curvature of the each curved portion is not less than 2 mm.

With this construction of the electrolyte 26", unwanted phenomenon in which the platinum electrodes 32 and 34 covering the curved portions come off during the coating process thereof does not occur. This is because the thickness of each platinum electrode on the electrolyte 26" can be uniform throughout to prevent the occurrence of the stress concentration in the platinum electrode at the each curved portion of the electrolyte during the platinum coating process.

Although, the present invention has been shown with reference to a few embodiments, it will be obvious to those skilled in the art that is not so limited, but is susceptible to various other changes and modifications without departing from the spirit thereof.

What is claimed is:

1. An oxygen sensor for determining oxygen concentration in a gas mixture, comprising:
    a solid-state axially elongated tubular electrolyte having an axial closed end and an axial open end;
    first and second electrodes respectively covering the outer and inner surfaces of said electrolyte, said second electrode defining a generally hollow chamber near said open end;
    means comprising a metallic holder for stationarily supporting said tubular electrolyte and said first and second electrodes, said holder being in electrical contact with said first electrode;
    an electrically conducting annular head member tightly disposed in said chamber;
    an electrically conducting elongated member including an elongated section of a diameter smaller than that of said chamber and a radially outwardly raised section of a diameter equal to that of said chamber, said elongated member being inserted into said chamber so that said elongated section to located between said annular head member and said raised section and said raised section is tightly engaged with said inner surface of said tubular electrolyte via said second electrode; and
    a corrugated, cylindrical metallic member coaxially disposed around said elongated section, the corrugations thereof being in contact with the outer surface of said elongated section and with the inner surface of said tubular electrolyte via said second electrode.

2. The oxygen sensor as claimed in claim 1, wherein said annular head member and said elongated member are respectively formed with through passages which are aligned with each other to provide a fluid communication between said chamber and the atmosphere.

3. The oxygen sensor as claimed in claim 2, wherein said annular head member is formed with a female portion into which a male portion formed on an end of said elongated section is tightly disposed.

4. The oxygen sensor as claimed in claim 1, wherein the cross-section of each corrugation of said corrugated cylindrical member comprises perpendicular and slanted portions with respect to the axis of said corrugated cylindrical member, whereby a saw-tooth configuration is defined.

5. The oxygen sensor as claimed in claim 1, wherein said closed end of said electrolyte has a wall thickness ranging from about 0.3 to 1.0 mm.

6. The oxygen sensor as claimed in claim 5, wherein the wall thickness of said electrolyte gradually decreases in the direction toward said closed end from said open end.

7. The oxygen sensor as claimed in claim 6, wherein each curved portion formed on said outer and inner surfaces of said electrolyte is smoothly rounded off.

8. The oxygen sensor as claimed in claim 7, wherein the radius of curvature of each curved portion is at least about 2 mm.

9. An oxygen sensor for determining oxygen concentration in a gas mixture flowing through a tube, comprising:
a metallic holder defining two open ends and a bore, one of said ends being coupled in an aperture formed in a wall portion of the tube, with the other end being directed outwardly from the tube;
a solid-state electrolyte shaped into a conical tube with a closed end and an open end having a larger diameter than that of said closed end, the wall thickness of said electrolyte gradually decreasing toward the closed end from the open end, said electrolyte being disposed in said metallic holder with the closed end thereof projecting into said tube, and the closed end having a wall thickness ranging from about 0.3 to 1.0 mm;
first and second electrodes respectively covering the outer and inner surfaces of the conical-shaped electrolyte, said first electrode being in contact with said metallic holder, and said second electrode defining a generally hollow chamber near said open end;
an electrically conducting annular head member tightly disposed in said chamber;
an electrically conducting elongated member including an elongated section of a diameter smaller than that of said chamber and a radially outwardly raised section of a diameter equal to that of said chamber, said elongated member being inserted into said chamber so that said elongated section is located between said annular head member and said raised section and said raised section is tightly engaged with the inner surface of said tubular electrolyte via said second electrode; and
a corrugated cylindrical metallic member coaxially disposed around said elongated section, the corrugations thereof being in contact with an outer surface of said elongated section and with the inner surface of said tubular electrolyte via said second electrode.

10. The oxygen sensor as claimed in claim 9, wherein said electrolyte and said first and second electrodes comprise a portion which projects into said tube to be exposed to said gas mixture, the axial length of said portion being at least about 12 mm.

11. The oxygen sensor as claimed in claim 10, wherein the cross-section of each corrugation of said corrugated cylindrical member comprises perpendicular and slanted portions with respect to the axis of said corrugated cylindrical member, whereby a saw-tooth configuration is defined.

* * * * *